US012699781B1

(12) United States Patent
Vasiliu-Feltes et al.

(10) Patent No.: US 12,699,781 B1
(45) Date of Patent: Aug. 4, 2026

(54) SYSTEMS AND METHODS FOR A MULTI-SYSTEM, MULTI-CLIENT, MULTI-DIRECTIONAL, CYBER- RESILIENT, AI-ENABLED, PERMISSIONED BLOCK-CHAIN PRECISION MEDICINE DATA EXCHANGE PLATFORM

(71) Applicant: SOFTHREAD, INC., Severna Park, MD (US)

(72) Inventors: Ingrid Vasiliu-Feltes, Miami, FL (US); Stephen Dennis, Columbia, MD (US); Eliot Siegel, Orlando, FL (US)

(73) Assignee: SOFTHREAD, INC., Severna Park, MD (US)

( * ) Notice: Subject to any disclaimer, the term of this patent is extended or adjusted under 35 U.S.C. 154(b) by 325 days.

(21) Appl. No.: 18/108,454

(22) Filed: Feb. 10, 2023

Related U.S. Application Data

(60) Provisional application No. 63/309,420, filed on Feb. 11, 2022.

(51) Int. Cl.
| | |
|---|---|
| *G06F 15/16* | (2006.01) |
| *G06F 21/60* | (2013.01) |
| *G06F 21/62* | (2013.01) |
| *G16H 10/60* | (2018.01) |

(52) U.S. Cl.
CPC ........ *G06F 21/602* (2013.01); *G06F 21/6245* (2013.01); *G16H 10/60* (2018.01)

(58) Field of Classification Search
CPC .... G06F 21/602; G06F 21/6245; G16H 10/60
See application file for complete search history.

(56) References Cited

U.S. PATENT DOCUMENTS

2021/0192346 A1* 6/2021 Taylor .................... G06N 3/088
2021/0350887 A1* 11/2021 Derosa-Grund ...... H04L 9/3247

* cited by examiner

*Primary Examiner* — Normin Abedin
(74) *Attorney, Agent, or Firm* — Kutak Rock LLP

(57) ABSTRACT

Techniques are described herein for enhancing the privacy, confidentiality, cyber-resilience, and operational efficiency of multi-system, multi-client, multi-directional precision medicine data exchanges among client users, devices, servers, cloud environments, or other applications within one network or a system of networks by deploying a permissioned blockchain, that uses threshold cryptographic primitives and the key component of permissioned blockchains called Byzantine fault-tolerant (BFT) protocol, combined with fine-grained access control, publish/subscribe capabilities and a novel use of the private chaincode functionality during precision medicine exchange operations, which involves image sharing without sacrificing performance. Techniques, methods, processes, and systems described herein can enhance operational efficiency by increasing operational processing speed and reducing operational processing time for precision medicine data exchange operations within the precision medicine platform.

2 Claims, 7 Drawing Sheets

ILLUSTRATION OF THE PROPOSED INVENTION: A MULTI-SYSTEM, MULTI-CLIENT, MULTI-DIRECTIONAL, CYBER-RESILIENT, PERMISSIONED BLOCKCHAIN PRECISION MEDICINE EXCHANGE PLATFORM (" workflow-agnostic)

FIGURE 1. ILLUSTRATION OF THE PROPOSED INVENTION: A MULTI-SYSTEM, MULTI-CLIENT, MULTI-DIRECTIONAL, CYBER-RESILIENT, PERMISSIONED BLOCKCHAIN PRECISION MEDICINE EXCHANGE PLATFORM (" workflow-agnostic)

Figure 2. ILUSTRATION OF A PERMISSIONED BLOCKCHAIN
NETWORK WITHIN THE PROPOSED SYSTEM

FIGURE 3. ILLUSTRATION OF KEY COMPONENTS FOR PROPOSED SYSTEM FOR AN INDUSTRY AGNOSTIC WORKLOW

FIGURE 5. Precision Medicine- Medical Imaging (Radiology) Workflow

Example

Precision Medicine Exchange-Application in Transplant Service: Workflow Example

Precision Medicine Exchange-Application in Genomics Medicine Services

SYSTEMS AND METHODS FOR A MULTI-SYSTEM, MULTI-CLIENT, MULTI-DIRECTIONAL, CYBER- RESILIENT, AI-ENABLED, PERMISSIONED BLOCK-CHAIN PRECISION MEDICINE DATA EXCHANGE PLATFORM

CROSS-REFERENCE TO RELATED APPLICATIONS

This application claims priority to U.S. Provisional Patent Application Ser. No. 63/309,420, filed Feb. 11, 2022, the entire disclosure of which is incorporated herein by reference.

FIELD OF THE INVENTION

The present invention disclosure relates generally to systems and methods for precision medicine data exchanges that may occur among systems of networks, one or more individual networks, servers, devices, cloud-enabled technology applications, and/or other embedded computing services. More specifically, the present invention is concerned with systems and methods for a multi-system, multi-client, multi-directional, cyber-resilient, zero trust permissioned blockchain infrastructure with decentralized, attribute-based, fine-grained access control, and confidentiality preserving precision medicine data exchange capabilities.

BACKGROUND

Precision Medicine is currently defined as "an emerging approach for disease treatment and prevention that takes into account individual variability in genes, environment, and lifestyle for each person". The precision medicine market size is estimated to reach USD 126.14 billion by 2025 and is expected to grow at 12.48% CAGR. Precision medicine has gained tremendous traction due to the recent pandemic, with several domains receiving increased funding and showcasing major scientific breakthroughs. The amount of data being generated and stored as a consequence of this increased activity has increased steadily and it is estimated that 30% of the world's data volume is being generated by the healthcare industry. By 2025, the compound annual growth rate of data for healthcare will reach 36%, At the same time, the key players in the global health arena are tasked to analyze these exponentially increasing data sets and generate valuable insights.

While numerous technologies such as AI and blockchain have been deployed to mine the data stored in electronic medical records or registries and one or more consortiums have joined forces to create meaningful data ex-changes, we are still experiencing barriers and challenges in the global health ecosystem. The key barriers and challenges include accurate and timely communication, data harmonization, data standardization, and multidirectional information flow which are all essential for the design, development, and deployment of novel precision medicine solutions. Furthermore, data governance challenges related to user access, user control, user consent, data integrity, data provenance, data stewardship, and data privacy remain to be solved in an effective and operationally efficient way.

One of the remaining barriers that must be addressed is the ability to share the full spectrum of data types re-quired for precision medicine solutions such as the exchange of medical images, advanced genomic sequencing data (whole genome and whole exome), biological specimen data stored in biobanks (tissues, blood, and derivatives, other body fluids, cells) and other metadata, in a secure, confidentiality and integrity preserving way while maintaining operational efficiency.

Traditional blockchain deployments have not been able to allow an efficient, secure, privacy and confidentiality preserving precision medicine data exchange among multiple users. Similarly, traditional federated learning models deployed in precision medicine are highly vulnerable to cyber-attacks. Traditional combined blockchain and federated learning deployments have also not been able to create a zero-trust environment for the exchange of medical images, whole-genome or whole-exome sequencing data, as well as biological specimen data collected and stored by large biobanks.

To be able to advance the new precision medicine discipline at the pace needed to solve major global public health challenges and fully leverage the rich data sets stored in the cloud to improve global population health, we must be able to deploy a cloud-enabled, yet cloud independent, easily scalable, secure, cyber-resilient precision medicine platform that leverages the unique features offered by blockchain technology and federated learning for all types of precision medicine data exchanges, among a plurality of user types and a vast number of devices, environments, and precision medicine information systems.

Building a zero-trust, blockchain, and AI-enabled precision medicine platform that combines collaborative learning with permissioned blockchain functionality, wherein a local model can be trained off-chain using its owner data, and then the improved updated model can be committed to the blockchain via encrypted communication as a transaction stored in an immutable ledger, could prove to be a paradigm-changing innovation. Different members who own the blockchain network would be able to combine, update, or even share the local model to train a global model to improve training accuracy. The patient-sensitive data would never need to be shared with different third parties because only the updates of the model would have to be shared in this zero-trust environment.

Our invention offers a solution for exchanging all types of precision medicine data, including medical images, whole genome or whole exome, other biological specimens stored in biobanks, and other metadata through a Multi-System, Multi-Client, Multi-Directional, Cyber-Resilient, AI-Enabled, Permissioned Blockchain Precision Medicine platform.

SUMMARY

The summary of the present disclosure is provided to introduce a selection of key concepts in a simplified format that are further addressed in the detailed description section below.

The approaches described in this section are approaches that could be pursued, but not necessarily approaches that have been previously conceived or pursued. Therefore, unless otherwise indicated, one should not assume that any of the approaches described in this section qualify as prior art merely by virtue of being included in this section.

The present disclosure addresses the need for an innovative, practical solution for managing secure precision medicine data exchange for instances where one or more different clients, one or more devices, one or more devices originating from different vendors, or clients and devices belonging to different systems of networks or networks, perhaps even using different operating systems, using different servers, using different cloud environments, using different fabric networks, or using different information management systems, need to have the ability to exchange one or more confidential precision medicine data in a privacy-preserving, integrity-preserving way, while maintaining operational speed and efficiency.

The present disclosure addresses the need for a precision medicine data exchange platform that can, in some embodiments, perform the full spectrum of needed services in a trust network, such as e-consenting, continuous user identification, fine-grained user access control, client certificates and policies for certificate verification, as well as have robust access control for the various client, device or image or nonimage data format types.

The present disclosure addresses the need for a precision medicine data exchange platform that can, in some embodiments, provide data provenance and record all transactions in an im-mutable way to enhance auditability and compliance for heavily regulated industries where highly protected precision medicine data have to be shared.

The present disclosure addresses the need for a precision medicine data exchange platform that can, in some embodiments, be industry-agnostic, server-agnostic, cloud environment-agnostic, device-agnostic, cloud enabled, and cloud-independent.

The present disclosure addresses the need for a precision medicine data exchange platform that can, in some embodiments, be easily scalable and interoperable with any technology infra-structure or information technology management system.

The present disclosure addresses the need for a precision medicine data exchange platform that can, in some embodiments, provide blockchain secure remote precision medicine data access.

The present disclosure addresses the need for a precision medicine data exchange platform that can, in some embodiments, provide automated permissioning and mapping for zero trust identity protection during precision medicine data exchange operations.

The present disclosure addresses the need for a precision medicine data exchange platform that can, in some embodiments, provide decentralized access control for zero-trust network identity protection during precision medicine data operations by offering publication/subscribe functionality.

The present disclosure addresses the need for a precision medicine data exchange platform that can, in some embodiments, provide fine-grained access control for zero-trust access control for precision medicine data operations.

The present disclosure addresses the need for a precision medicine data exchange platform that can, in some embodiments, provide the ability to secure digital precision medicine data identities at scale.

The present disclosure addresses the need for a precision medicine data exchange platform that can, in some embodiments, provide dynamic security for cloud-based precision medicine data.

The present disclosure addresses the need for a precision medicine data exchange platform that can, in some embodiments, provide the ability to provide data provenance for precision medicine data exchanged.

The present disclosure addresses the need for a precision medicine exchange platform that can, in some embodiments, provide immutability of image metadata exchange operations using a tamper-proof blockchain system. Multiple separate parties converge to a single immutable record of images using a decentralized consensus mechanism without requiring central authorization.

The present disclosure addresses the need for a precision medicine data exchange platform that can, in some embodiments, enhance operational efficiency during precision medicine exchange operations by deploying full private chaincode and smart contracting functionalities.

The present disclosure addresses the need for a precision medicine data exchange platform that can, in some embodiments, provide integrity and confidentiality by the deployment of a permissioned blockchain technology that uses threshold cryptographic primitives and enhanced security using Byzantine fault-tolerant (BFT) protocols, combined with a novel application of private chaincode functionality for precision medicine data exchange operations.

The present disclosure addresses the need for federated learning combined with a unique private blockchain channel for access control to enhance security.

The present disclosure addresses the need for federated learning model combined with a unique private blockchain channel to allow collaborative training of the model and enhance the accuracy of the model off chain.

The invention described in the present disclosure is configured for the use of confidentiality and integrity-protected chaincodes that define the application. Within the precision medicine platform described, the confidentiality and integrity of precision medicine exchange operations and their related data are executed on a CPU in a trusted execution environment using contexts called enclaves. These enclaves executed on a CPU are secure and protected because they isolate data and programs from the host operating system and hypervisor (computer software or hardware that runs a virtual machine) in hardware, even if the entire platform is compromised. Within the precision medicine platform described in the present disclosure, precision medicine data such as genomics data, biological specimen data, medical imaging data are not stored onchain, and chain codes encrypt all other necessary image-related data (metadata) stored on the ledger. Within the precision medicine platform described the cryptography hash of images as image identities and their owner's digital signature are stored on the ledger. Within the precision medicine platform described in the present disclosure, protected chaincode executed in enclaves are programmed and verified to process and/or release data according to specific and fully customizable requirements or rules that can, in certain embodiments, be required in any industry.

The present disclosure is differentiated from all other precision medicine data exchange platforms that require the upload, download, and exchange of the actual genomics, biological specimens, medical imaging data, which can, in some embodiments, increase the cyber risk and reduce privacy, as well as decrease operational efficiency. The proposed solution can utilize chaincode (such as Hyperledger) as one of the components specifically targeting operational efficiency between different parties. Different systems and users can efficiently and collaboratively share the image hash code in one ledger to improve the efficiency of image sharing without sacrificing performance. Moreover, our proposed solution does not require any authentications or a cryptographic library to maintain a trusted channel between any of the organizations before exchanges can occur since each member engaged in the exchange has been authorized before joining.

The present disclosure can, in some embodiments, offer a novel practical solution for precision medicine data exchanges that provides all the above features and functionalities for any type of confidential, secure precision medicine exchange workflows that can be performed within a multi-system, multi-client, multi-directional network or system of networks that can accommodate a multitude of user workflows within each industry.

The foregoing and other objects are intended to be illustrative of the invention and are not meant in a limiting sense. Many possible embodiments of the invention can, in some embodiments, be made and will be readily evident upon a study of the following specification and accompanying drawings comprising a part thereof. Various features and subcombinations of invention can, in some embodiments, be employed without reference to other features and subcombinations. Other objects and advantages of this invention will become apparent from the following description taken in connection with the accompanying drawings, wherein is set forth by way of illustration and example, an embodiment of this invention and various features thereof.

A preferred embodiment of the invention, illustrative of the best mode in which the applicant has contemplated applying the principles, is set forth in the following description and is shown in the drawings and is particularly and distinctly pointed out and set forth in the appended claims.

BRIEF DESCRIPTION OF THE DRAWINGS

A preferred embodiment of the invention, illustrative of the best mode in which the applicant has contemplated applying the principles, is set forth in the following description and is shown in the drawings and is particularly and distinctly pointed out and set forth in the appended claims.

DETAILED DESCRIPTION

Figure 1:
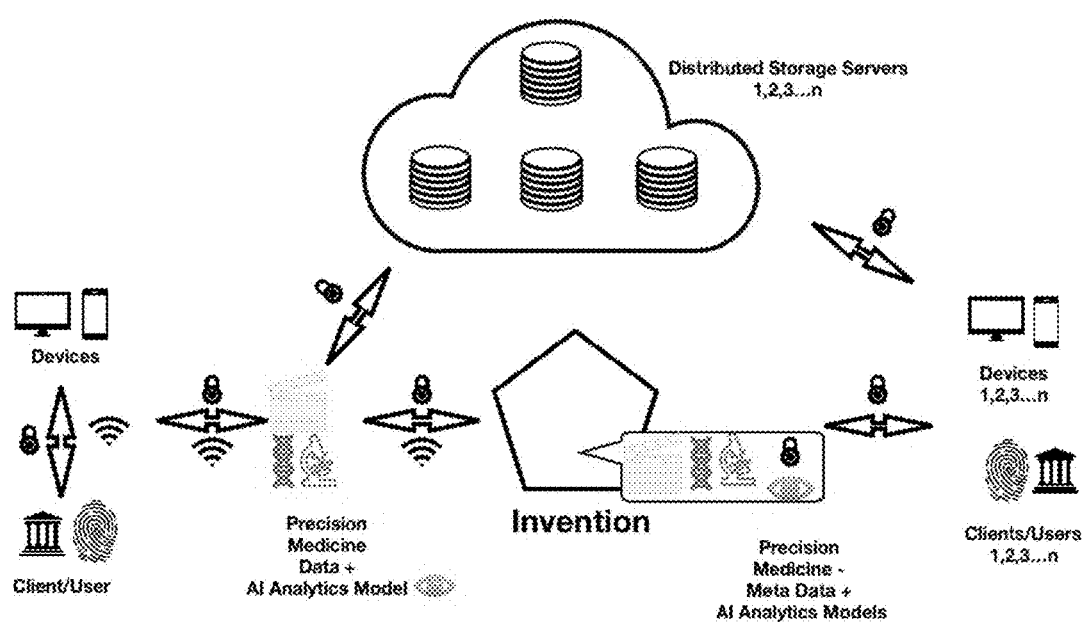
FIG. 1 illustrates an environment representing an example of a Multi-System, Multi-Client, Multi-Directional, Cyber-Resilient, Permissioned Blockchain Precision Medicine Exchange Platform applicable for any industry.
Figure 2:
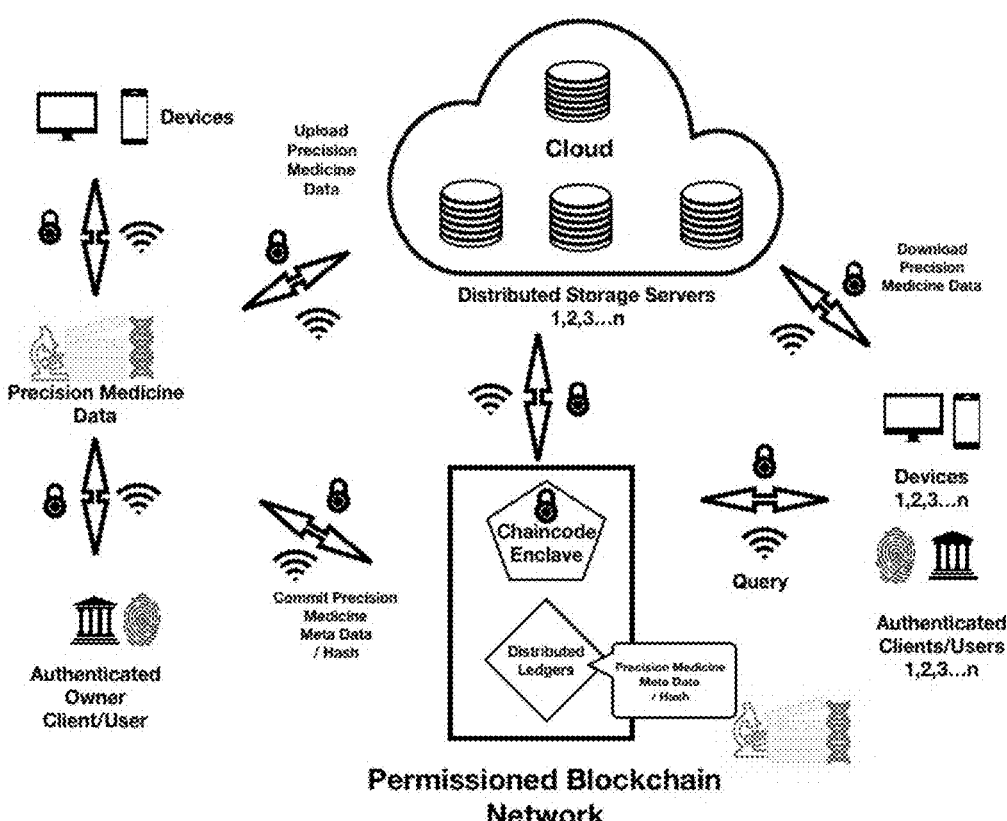
FIG. 2 illustrates the Permissioned Blockchain Network which can include but not be limited to at least one server, one device, one owner client, one user, more than one server, a distributed ledger, a chaincode enclave, a hash, a chaincode, etc.
Figure 3:
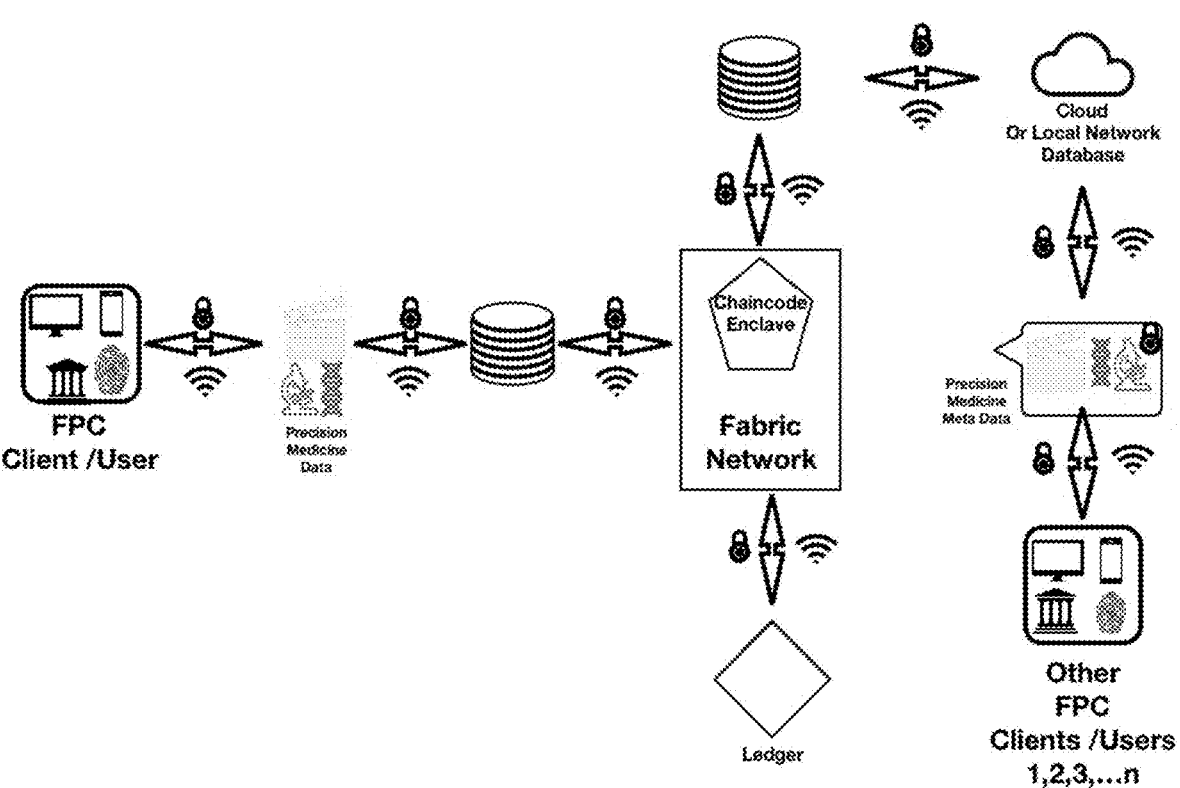
FIG. 3 illustrates an industry-agnostic workflow for at least one precision medicine exchange among at least one Fabric Private Chaincode (FPC) Client/User (originator) and other FPC client users (1, 2, 3, . . . , n), and at least one server, a fabric network, one ledger, one enclave, a cloud environment, at least one image, one biological specimen, one genomics data set etc.
Figure 4:
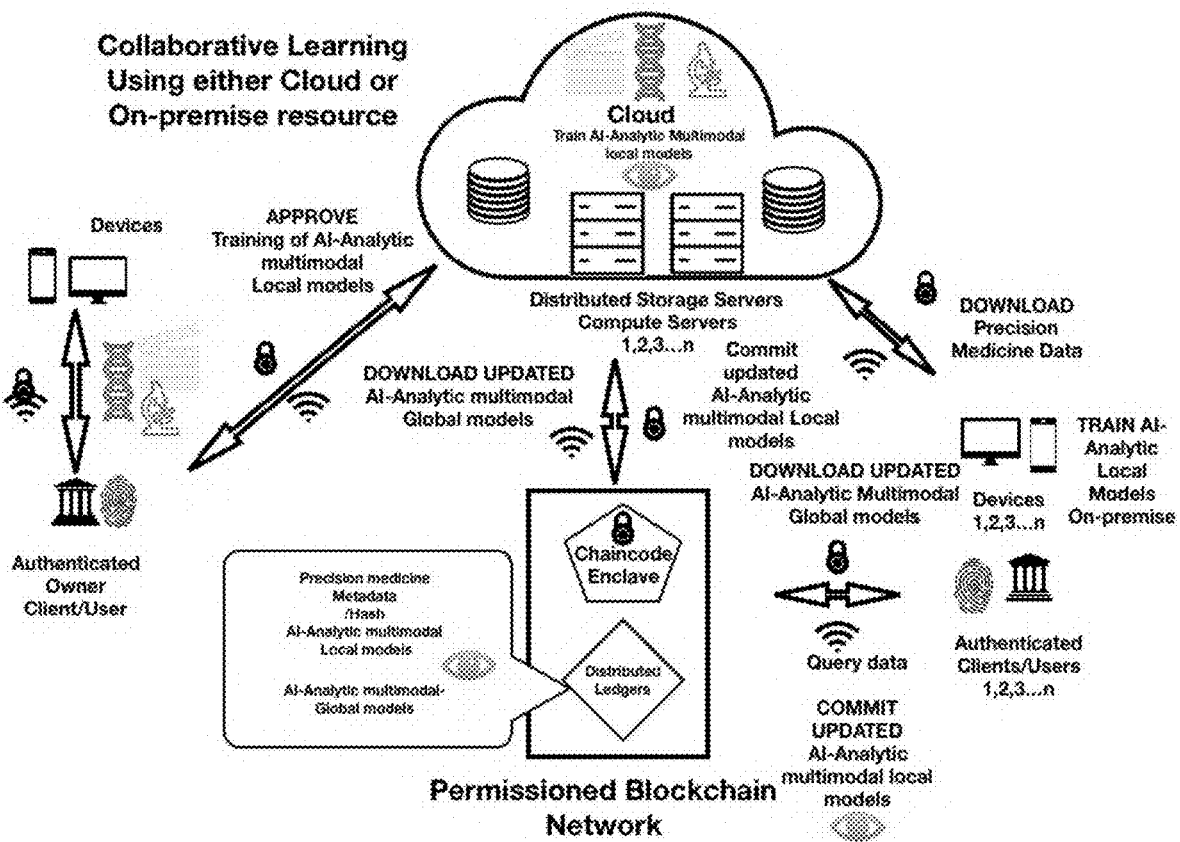
FIG. 4 illustrates a collaborative Federated Learning workflow, using either Cloud or On-premise resources.
Figure 5:
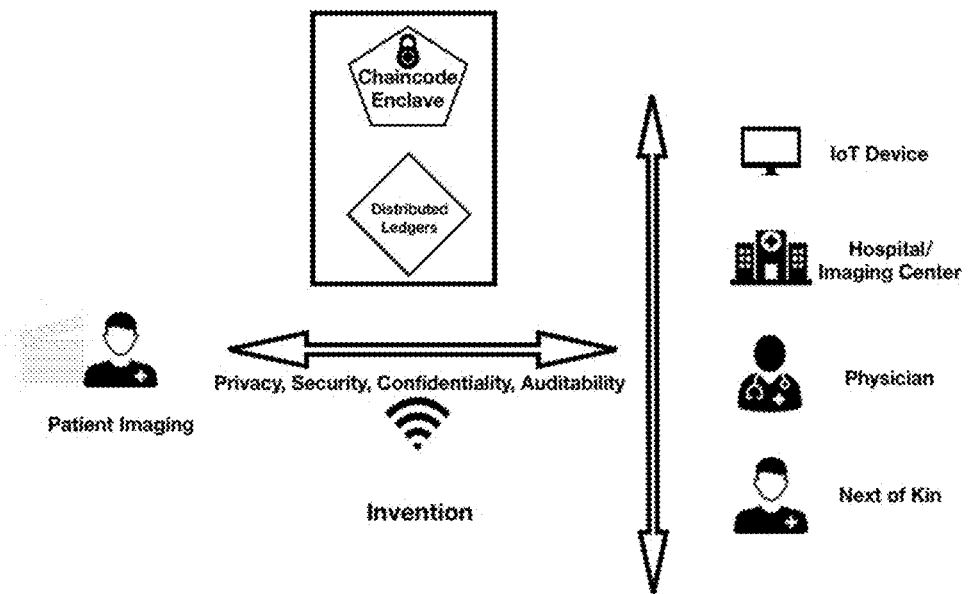
FIG. 5 illustrates a sample precision medicine exchange workflow for how at least one medical image (radiology) is exchanged between at least one patient, one physician, one next of kin, one IoT device and one hospital or imaging center.
Figure 6:
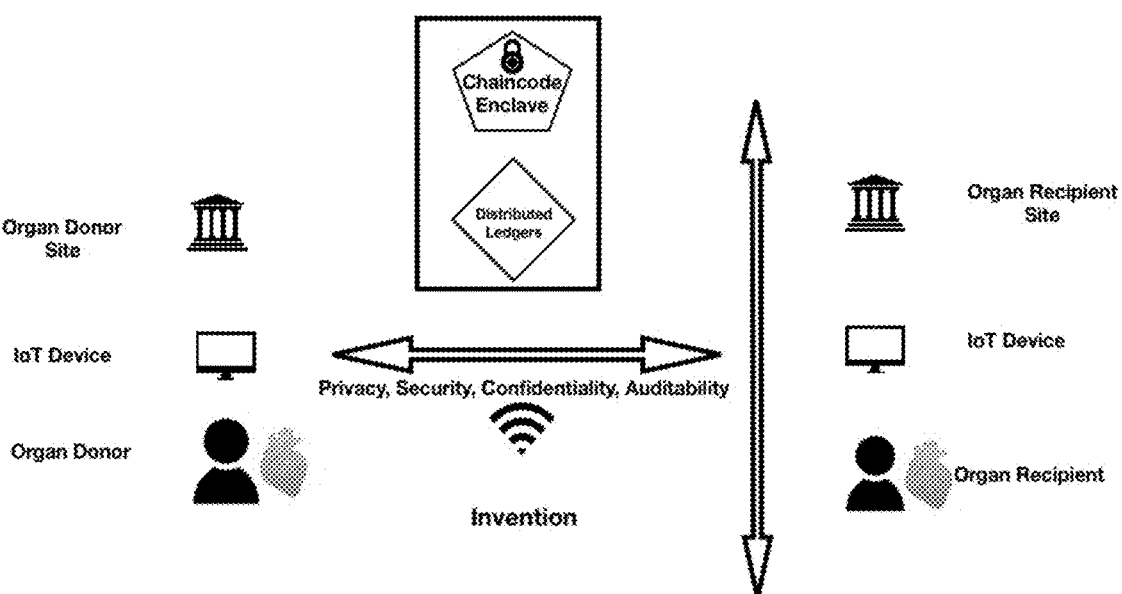
FIG. 6 illustrates a Precision Medicine-Organ Donation/Transplant Workflow Example.
Figure 7:
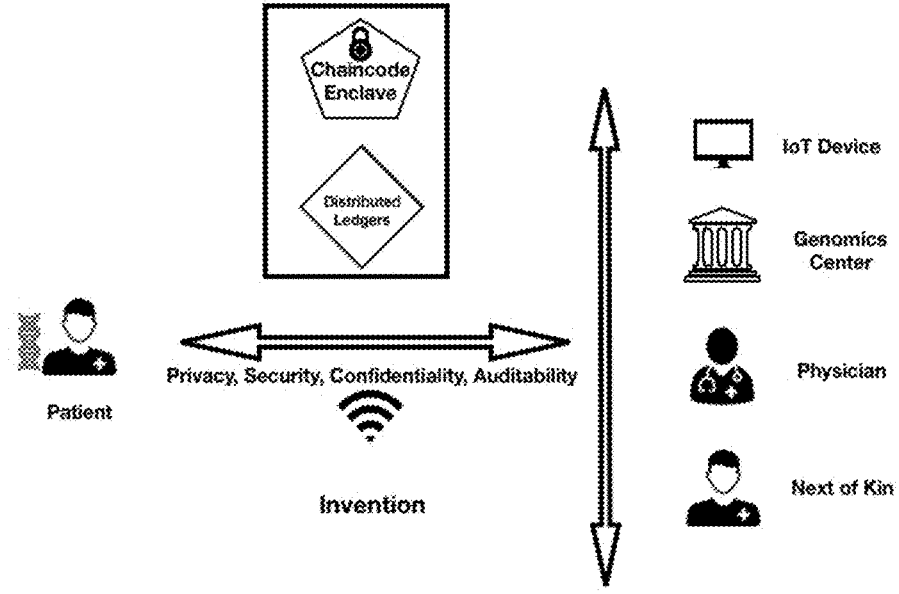
FIG. 7 illustrates Precision Medicine-Genomics Services Workflow Example.

As required, a a detailed embodiment of the present invention is disclosed herein; however, it is to be understood that the disclosed embodiment is merely exemplary of the principles of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The following detailed description includes references to the accompanying drawings, which form a part of the detailed description. The drawings show illustrations in accordance with the exemplary embodiments. These exemplary embodiments, which are also referred to herein as "examples" are described in enough detail to enable those skilled in the art to practice the present subject matter. The embodiments can be combined and other embodiments can be utilized, or structural, logical, and technical changes can be made without departing from the scope of what is claimed. Features of the embodiments described in one example can be combined with features described in a different example. The following detailed description is, therefore, not to be taken in a limiting sense, and the scope is defined by the appended claims and their equivalents. With the following description, for the purposes of explanation, numerous specific details are set forth to provide a thorough understanding. One or more examples can be practiced without these specific details. In some examples, well-known structures and devices are described with reference to the drawings to avoid unnecessarily obscuring features and characteristics of the presently described examples. This specification may include, and the claims may recite, some examples beyond those that are described in this introductory paragraph.

The examples described herein are differentiated from all previously existing technology, such as but not limited to the ability to share images peer to peer without the need for a formal facility business agreement, the ability of a user to determine specifically whom he/she can share precision medicine data with, ability to create an audit trail accessible by the patient or anyone the patient chooses have access to it, the ability to provide more rapid sharing in emergencies, etc.

Examples described herein include a technology platform that can include these primary components: user/client, IoT device, server, network, cloud computing platform, blockchain network, chaincode, node, hash, distributed ledger, secure private channel, smart contract, artificial intelligence algorithm, consensus algorithm, programming language, application programming interface, user interface, image acquisition device imaging modalities, raw (unprocessed) precision medicine exchange such as a CT sinogram or K-space MRI data. Precision medicine exchanges can include accessing, sending, and receiving functionality, and the precision medicine exchanges can include a processor, an image acquisition device, image viewing devices, a specific communication protocol, an IP address, a cloud-based access system, specialized software, storage devices, images of any type and format, including formats for a variety of medical modalities such as radiology, nuclear medicine, cardiology, pathology, dermatology, ophthalmology, surgery, GI medicine, and others in formats such as DICOM, JPG, PNG and compressed data formats such as cosine transform and wavelets.

Examples can, in some embodiments, include commercial and industry-relevant devices for hospital systems, hospitals, clinics, ambulatory surgical centers, transplant centers, blood banks, organ donor networks, laboratory centers, imaging centers, fertility centers, maternity or birthing centers, health plans, etc.

In some embodiments, the system and method can include other technology infrastructure used for precision medicine exchanges such as screens, processors, picture archival systems, vendor neutral archives, picture communication systems, data storage systems, digital imaging systems, digital communication system, algorithms, film or paper digitization, analytics platforms, local area network (LAN), wide area network (WAN), Ethernet network, Token Ring network, asynchronous transfer mode (ATM) network, Wi-Fi network, Bluetooth, the Internet, cellular telephone network, Enhanced Data rates for GSM Evolution (EDGE) network, long-term evolution (LTE) network, 5G, 6G, infrared, satellite network, or other computing communications networks.

In some embodiments, the system and methods can include a network of nodes. The nodes can be local to and/or remote from each other.

In some embodiments, the system and method can include, one or more programming languages such as Python, SQL, NoSQL, C#, Rust, Perl, Go, JavaScript, HTML, CSS, Java, etc.

Examples can include, in some embodiments, one or more cloud computing environments (IBM, Microsoft, Amazon, Ambra, GE, Dell, Siemens, Philips, Canon.)

Examples can include, in some embodiments, a variety of standards used in industries performing confidential precision medicine exchanges such as HL7, FHIR, DICOM, CCD, DFARS, FISMA, ISO, HIPAA, GeoTiff, EOSAT, CEOS, LGSOWG, and HDF, etc.

Examples can include, in some embodiments, a variety of APIs, API architecture types, and protocols.

Examples can include, in some embodiments, devices that can be mobile applications, stationary or portable devices, stationary of portable microcomputers, web-based applications, etc.

Techniques, methods, processes, and systems described herein can enhance privacy, security, the confidentiality of precision medicine exchanges among multiple devices, multiple clients, multiple servers, multiple environments, multiple information technology systems, multiple networks, or systems of networks.

Examples can include, in some embodiments, various blockchain technologies or blockchain frameworks used in a variety of industries such as Hyperledger, Ethereum, R3 Corda, Ripple, Quorum, Hyperledger Sawtooth, Hyperledger Fabric, IBM Blockchain, etc.

Examples can include, in some embodiments, a network or system of networks. A network can be physical or an overlay network. Networks can use various resources, such as include a processor, data storage, a virtual machine, a container, and/or a software application. Network resources are shared among multiple clients which can request services from the network concomitantly and independently of each other. Networks can be cloud-based and would include a variety of service models.

Examples can include, in some embodiments, a variety of cloud-based networks such as public, private, or hybrid cloud networks.

Examples can include, in some embodiments, a variety of operating systems, such as Microsoft Windows, Apple macOS, Ubuntu, Android, Apple IOS, etc, Fedora, Solaris, Free BSD, Chrome OS, CentOS, Debian, Deepin, etc.

Techniques, methods, processes, and systems described herein can, in some embodiments, enhance operational efficiency by increasing operational processing speed and reducing operational processing time.

The precision medicine platform described in the present disclosure, can in some embodiments, demonstrates an innovative multi-system, multi-client, multi-directional precision medicine data exchange that can offer a transparent, decentralized trust network or system of networks for any protected precision medicine data exchanges. The trust network or system of networks can offer optimal privacy, confidentiality, and security, as well as advanced identity management via e-consenting, and fine-grained access control. The precision medicine platform can enable compliance and auditability via immutability, and data provenance. The precision medicine platform is configured to be industry agnostic, network agnostic, system-agnostic, server-agnostic, device-agnostic, image type-agnostic, workflow-agnostic, device-agnostic, and to be cloud-independent, and cloud-enabled. The trust network or system of networks can be highly interoperable with multiple fabric blockchain networks, easily scalable, and can optimize security via integrity-protected private chaincode functionality.

The precision medicine platform described in the present disclosure can create a trusted, decentralized, and immutable e-consenting system for all clients utilizing the precision medicine exchange platform.

The precision medicine platform described in the present disclosure can, in some embodiments, allow for self-sovereignty of image sharing for all clients utilizing the precision medicine exchange platform.

The precision medicine platform described in the present disclosure can, in some embodiments, optimize digital identity management for all precision medicine exchange workflows.

The precision medicine platform described in the present disclosure can, in some embodiments, enhance network access management by deploying fine-grained access control and pub/sub capabilities for all precision medicine exchange operations and workflows.

The precision medicine platform described in the present disclosure can, in some embodiments, enhance privacy.

The precision medicine platform described in the present disclosure can, in some embodiments, enhance confidentiality.

The precision medicine platform described in the present disclosure can, in some embodiments, enhance auditability.

The precision medicine platform described in the present disclosure can, in some embodiments, enhance security.

The precision medicine platform described in the present disclosure can, in some embodiments, enable compliance.

The precision medicine platform described in the present disclosure can, in some embodiments, maximize data integrity.

The precision medicine platform described in the present disclosure can, in some embodiments, maximize data provenance.

The precision medicine platform can, in certain embodiments, use asynchronous binary agreement (ABA) and adaptive threshold signature for data provenance. All the transactions need to be proved and signed before commit to the immutable ledger.

The precision medicine platform described in the present disclosure can, in some embodiments, optimize the operational efficiency of precision medicine exchanges by allowing off chain storage of the actual image and by only storing all other related data onchain.

The precision medicine platform described in the present disclosure can, in some embodiments, optimize speed of precision medicine exchanges by utilizing smart contract functionality.

The precision medicine platform described in the present disclosure can, in some embodiments, utilize fabric private chaincode (FPC) functionality.

The precision medicine platform described in the present disclosure is configured to not store any of the actual precision medicine data such as images or biologic specimens or genomic data onchain.

The precision medicine platform described in the present disclosure is configured to store all other image-related metadata, cryptography hash of image, and owner's digital signatures onchain.

The precision medicine platform described in the present disclosure is configured for the use of confidentiality and integrity protected chaincodes.

Within the precision medicine platform described in the present disclosure chaincodes are executed in an enclave and execution is protected from the operating system and the hypervisor.

Within the precision medicine platform described in the present disclosure chaincodes encrypt data stored on the ledger.

Within the precision medicine platform described in the present disclosure the FPC chaincode establishes a secure channel.

Within the precision medicine platform described in the present disclosure enclaves protect data even with the fabric blockchain network.

Within the precision medicine platform described in the present disclosure enclaves are programmed and verified to process and release data according to specific and fully customizable requirements or rules.

The precision medicine platform described in the present disclosure creates cryptographic encryption for key and value pairs.

The precision medicine platform described in the present disclosure described in the present disclosure is configured for optional AI-enablement [0055] The precision medicine platform described in the present disclosure can, in some embodiments, allow a variety of multi-system and multi-client precision medicine data exchange workflows.

The precision medicine platform described in the present disclosure can, in some embodiments, allow multi-directional precision medicine exchange workflows.

The precision medicine platform described in the present disclosure can, in some embodiments, allow a variety of operations and functions to occur concomitantly.

The precision medicine platform described in the present disclosure can, in some embodiments, allow precision medicine exchanges among a multitude of clients, devices, servers, environments, and networks or systems of networks.

The precision medicine exchange platform described in the present disclosure is cloud-enabled and cloud independent.

The precision medicine exchange platform described in the present disclosure is environment and device agnostic.

The precision medicine exchange platform described in the present disclosure can, in some embodiments, function as an overlay with other information technology systems.

The precision medicine exchange platform described in the present disclosure can, in some embodiments, be interoperable with any of the blockchain frameworks.

The precision medicine exchange platform described in the present disclosure is configured to be image type-agnostic (DICOM, APNG, AVIF, JPEG, GIF, RAW, TIFF, BMP, PSD, SVG, PDF, EPS, AI, CDR, WebP, ICO, etc.)

Fabric private Chain Code (FPC) enables the execution of chaincodes inside a trusted execution environment (TEE) and a trusted ledger enclave to provide confidentiality and integrity for the precision medicine exchange platform. Since chaincode is vulnerable to be attacked, the image metadata can be securely encrypted and hidden from any participants or even system administrator through TEE and trusted ledgers.

The precision medicine exchange platform does not store any of the actual images onchain.

The precision medicine exchange platform is storing all other image-related protected metadata onchain.

The fabric private chaincode (FPC) executes chaincodes in an enclave Fabric Private Chaincode (FPC) enables the execution of chaincodes inside a trusted execution environment (TEE) and a trusted ledger enclave, for example particularly using Intel Software Guard Extensions (SGX) to protect the privacy and security of chaincodes and computation from potentially untrusted peer nodes, members or organizations.

Enclaves protect client data even within the fabric network.

The enclave is a separated and encrypted region for codes and data in, for example, an intel CPU. The enclave can only be decrypted inside the processor, so it is even safe from direct reads from the RAM. It protects the data even within the fabric network. Enclaves isolate data and programs from the host operating system in hardware, meaning that all the chaincodes executing on the operating system are isolated from other applications, processors, threads, and operating systems as well as hypervisor which controls multiple operating systems to operate concurrently on a single hardware platform.

FPC chaincodes encrypt data stored on the ledger.

FPC chaincodes encrypt data stored on the ledger, and allow a programmer to write chaincode applications where the data is encrypted on the ledger and can only be accessed by authorized parties.

Client FPC chaincode establishes a secure channel.

FPC establishes a secure SGX-based enclave for executing private chaincode and all the released FPC client data will be encrypted stored in a ledger in a channel shared with different organizations.

A Fabric channel is a private subnet of communication between two or more specific network members or organizations, for the purpose of conducting private and confidential transactions.

Enclaves are programmed and verified to process and release data according to specific requirements (regulatory, business rules, clinical rules, other custom criteria).

The chaincodes execution in an enclave is a separated and encrypted region for code and data. Chaincodes can be programmed and verified to process and release data according to specific requirements (regulatory, business rules, clinical rules, other custom criteria).

Enhanced privacy, security, and confidentiality of collaborative learning as the model can be trained off-chain.

Different clients who are part of the network can combine, update, even share the local model to train a global model to improve its accuracy in an iterative manner.

After the local model is trained off chain, the updated model can be committed to the blockchain as a transaction stored in an immutable ledger Precision medicine data exchanges can, in some embodiments, include any combination type of medical data such as but not limited to HL7 data, genomic data files (FASTA, BED, GTF2, GFF3, BioSCOOP, or the like), biological specimen data, medical imaging data.

Precision medicine data exchanges can, in some embodiments, include any combination type of data such as HL7, biological specimen, genomic data, medical imaging etc.

The model used for collaborative learning can, in some embodiments, also include any combination of data, such as HL7, genomic data, biological specimen, medical imaging data, etc. (multimodal model).

The platform can, in some embodiments, have the capability to select the most relevant feature based on any combination of data included such as HL7, genomic data, biological specimen, medical imaging data, etc.

Techniques, methods, processes, and systems described herein can enhance operational efficiency by increasing operational processing speed and reducing operational processing time.

Various embodiments of the computer program, system, and method of embodiments of the present invention are implemented in hardware, software, firmware, or combinations thereof, which broadly comprises server devices, computing devices, and a communications network. Various embodiments of the server devices include computing devices that provide access to one or more general computing resources, such as Internet services, electronic mail services, data transfer services, and the like. In some embodiments the server devices also provides access to a database that stores information and data, with such information and data including, without limitation, account information, NLU model information, campaign information, personality information, or other information and data necessary and/or desirable for the implementation of the computer program, system, and method of the present invention, as will be discussed in more detail below.

Various embodiments of the server devices and the computing devices include any device, component, or equipment with a processing element and associated memory elements. In some embodiments the processing element implements operating systems, and in some such embodiments is capable of executing the computer program, which is also generally known as instructions, commands, software code, executables, applications (apps), and the like. In some embodiments the processing element includes processors, microprocessors, microcontrollers, field programmable gate arrays, and the like, or combinations thereof. In some embodiments the memory elements are capable of storing or retaining the computer program and in some such embodiments also store data, typically binary data, including text, databases, graphics, audio, video, combinations thereof, and the like. In some embodiments the memory elements also are known as a "computer-readable storage medium" and in some such embodiments include random access memory (RAM), read only memory (ROM), flash drive memory, floppy disks, hard disk drives, optical storage media such as compact discs (CDs or CDROMs), digital video disc (DVD), Blu-Ray™, and the like, or combinations thereof. In addition to these memory elements, in some embodiments the server devices further include file stores comprising a plurality of hard disk drives, network attached storage, or a separate storage network.

Various embodiments of the computing devices specifically include mobile communication devices (including wireless devices), work stations, desktop computers, laptop computers, palmtop computers, tablet computers, portable digital assistants (PDA), smart phones, wearable devices and the like, or combinations thereof. Various embodiments of the computing devices also include voice communication devices, such as cell phones or landline phones. In some preferred embodiments, the computing device has an electronic display, such as a cathode ray tube, liquid crystal display, plasma, or touch screen that is operable to display visual graphics, images, text, and the like. In certain embodiments, the computer program of the present invention facilitates interaction and communication through a graphical user interface (GUI) that is displayed via the electronic display. The GUI enables the user to interact with the electronic display by touching or pointing at display areas to provide information to the user control interface, which is discussed in more detail below. In additional preferred embodiments, the computing device includes an optical device such as a digital camera, video camera, optical scanner, or the like, such that the computing device can capture, store, and transmit digital images and/or videos.

In some embodiments the computing devices includes a user control interface that enables one or more users to share information and commands with the computing devices or server devices. In some embodiments, the user interface facilitates interaction through the GUI described above or, in other embodiments comprises one or more functionable inputs such as buttons, keyboard, switches, scrolls wheels, voice recognition elements such as a microphone, pointing devices such as mice, touchpads, tracking balls, styluses. Embodiments of the user control interface also include a speaker for providing audible instructions and feedback. Further, embodiments of the user control interface comprise wired or wireless data transfer elements, such as a communication component, removable memory, data transceivers, and/or transmitters, to enable the user and/or other computing devices to remotely interface with the computing device.

In various embodiments the communications network will be wired, wireless, and/or a combination thereof, and in various embodiments will include servers, routers, switches, wireless receivers and transmitters, and the like, as well as electrically conductive cables or optical cables. In various embodiments the communications network will also include local, metro, or wide area networks, as well as the Internet, or other cloud networks. Furthermore, some embodiments of the communications network include cellular or mobile phone networks, as well as landline phone networks, public switched telephone networks, fiber optic networks, or the like.

Various embodiments of both the server devices and the computing devices are connected to the communications network. In some embodiments server devices communicate with other server devices or computing devices through the communications network. Likewise, in some embodiments, the computing devices communicate with other computing devices or server devices through the communications network. In various embodiments, the connection to the communications network will be wired, wireless, and/or a combination thereof. Thus, the server devices and the computing devices will include the appropriate components to establish a wired or a wireless connection.

Various embodiments of the computer program of the present invention run on computing devices. In other embodiments the computer program runs on one or more server devices. Additionally, in some embodiments a first portion of the program, code, or instructions execute on a first server device or a first computing device, while a second portion of the program, code, or instructions execute on a second server device or a second computing device. In some embodiments, other portions of the program, code, or instructions execute on other server devices as well. For example, in some embodiments information is stored on a memory element associated with the server device, such that the information is remotely accessible to users of the computer program via one or more computing devices. Alternatively, in other embodiments the information is directly stored on the memory element associated with the one or more computing devices of the user. In additional embodiments of the present invention, a portion of the information is stored on the server device, while another portion is stored on the one or more computing devices. It will be appreciated that in some embodiments the various actions and calculations described herein as being performed by or using the computer program will actually be performed by one or more computers, processors, or other computational devices, such as the computing devices and/or server devices, independently or cooperatively executing portions of the computer program.

A user is capable of accessing various embodiments of the present invention via an electronic resource, such as an application, a mobile "app," or a website. In certain embodiments, portions of the computer program are embodied in a stand-alone program downloadable to a user's computing device or in a web-accessible program that is accessible by the user's computing device via the network. For some embodiments of the stand-alone program, a downloadable version of the computer program is stored, at least in part, on the server device. A user downloads at least a portion of the computer program onto the computing device via the network. After the computer program has been downloaded, the program is installed on the computing device in an executable format. For some embodiments of the web-accessible computer program, the user will simply access the computer program via the network (e.g., the Internet) with the computing device.

In the foregoing description, certain terms have been used for brevity, clearness and understanding; but no unnecessary limitations are to be implied therefrom beyond the requirements of the prior art, because such terms are used for descriptive purposes and are intended to be broadly construed. Moreover, the description and illustration of the inventions is by way of example, and the scope of the inventions is not limited to the exact details shown or described.

Although the foregoing detailed description of the present invention has been described by reference to an exemplary embodiment, and the best mode contemplated for carrying out the present invention has been shown and described, it will be understood that certain changes, modification or variations can, in some embodiments, be made in embodying the above invention, and in the construction thereof, other than those specifically set forth herein, can, in some embodiments, be achieved by those skilled in the art without departing from the spirit and scope of the invention, and that such changes, modification or variations are to be considered as being within the overall scope of the present invention. Therefore, it is contemplated to cover the present invention and any and all changes, modifications, variations, or equivalents that fall with in the true spirit and scope of the underlying principles disclosed and claimed herein. Consequently, the scope of the present invention is intended to be limited only by the attached claims, all matter contained in the above description and shown in the accompanying drawings shall be interpreted as illustrative and not in a limiting sense.

Having now described the features, discoveries and principles of the invention, the manner in which the invention is constructed and used, the characteristics of the construction, and advantageous, new and useful results obtained; the new and useful structures, devices, elements, arrangements, parts and combinations, are set forth in the appended claims.

It is also to be understood that the following claims are intended to cover all of the generic and specific features of the invention herein described, and all statements of the scope of the invention which, as a matter of language, might be said to fall therebetween.

What is claimed is:

1. A permissioned blockchain technology precision medicine system,
including:
a plurality of precision medicine data exchanges with off-chain image or biologic specimen or genomics storage, including precision medicine metadata that is cryptography hashed, and wherein the owner's digital signature is stored onchain;
an enclave isolated from the Operating System and Hypervisor;
a plurality of private channels connecting a plurality of blockchain networks;
identity management via e-consenting and self-sovereignty for image sharing and access control which provides control of precision medicine data access;
decentralized access control for zero-trust network identity protection during precision medicine data exchange operations by offering publication/subscribe functionality;
a permissioned blockchain that uses threshold cryptographic primitives and a Byzantine fault-tolerant (BFT) protocol, combined with private chaincode functionality for precision medicine exchange operations;
wherein said precision medicine data exchange operations are recorded to an immutable ledger;
wherein chaincodes executed on said enclave are isolated from the Operating System and Hypervisor;
wherein said precision medicine data exchanges include data provenance functionality, private chaincode functionality, secure and off-chain precision medicine data storage, and efficient multi-trust without complicated authentication through blockchain.

2. A system for sharing medicine data comprising:
A plurality of clients;
a device;
a server;
network or system of networks;
a cloud computing platform;
a fabric permissioned blockchain network to provide ledger services to a variety of users and applications,
an enclave isolated from an operating system and hypervisor;
a node;
a hash;
a distributed ledger;
a private channel;
a smart contract;
a consensus algorithm;
a programming language;
an application programming interface; and
a user interface,
wherein said ledger is configured to commit only cryptographic hashes and metadata associated with precision medicine data while the precision medicine data remains off chain.

* * * * *